United States Patent [19]

Howard, Jr.

[11] 4,101,594
[45] Jul. 18, 1978

[54] METHOD FOR DRYING A HYDROCARBON CONVERSION APPARATUS

[75] Inventor: Leroy J. Howard, Jr., Des Plaines, Ill.

[73] Assignee: UOP Inc., Des Plaines, Ill.

[21] Appl. No.: 755,373

[22] Filed: Dec. 19, 1976

[51] Int. Cl.$^2$ .......................... C07C 7/12; C07C 5/00
[52] U.S. Cl. ............................ 260/668 A; 260/668 R; 260/674 SA; 260/671 R; 208/DIG. 2; 208/310 Z
[58] Field of Search ............... 260/668 A; 208/310 Z, 208/143

[56] References Cited
U.S. PATENT DOCUMENTS

| | | | |
|---|---|---|---|
| 3,201,491 | 8/1965 | Stine et al. | 260/674 SA |
| 3,529,030 | 9/1970 | Chin | 208/361 |
| 3,626,020 | 12/1971 | Neuzil | 260/674 SA |
| 3,696,107 | 10/1972 | Neuzil | 260/674 SA |
| 3,825,490 | 7/1974 | Vachuda | 208/310 Z |
| 3,873,440 | 3/1975 | Hallman | 208/165 |
| 4,008,289 | 2/1977 | Ward et al. | 260/671 R |

Primary Examiner—Veronica O'Keefe
Attorney, Agent, or Firm—James R. Hoatson, Jr.; John F. Spears, Jr.; William H. Page, II

[57] ABSTRACT

A hydrocarbon conversion apparatus is dried as a preliminary step of a startup procedure by the circulation of a superheated vapor stream which is formed in one of two reboilers attached to a fractionation column used in the process. Preferably this vapor stream is formed on the tube side of the reboiler, with normal on-stream operation comprising the generation of the vapors fed to the column on the shell side of the reboiler.

11 Claims, 1 Drawing Figure

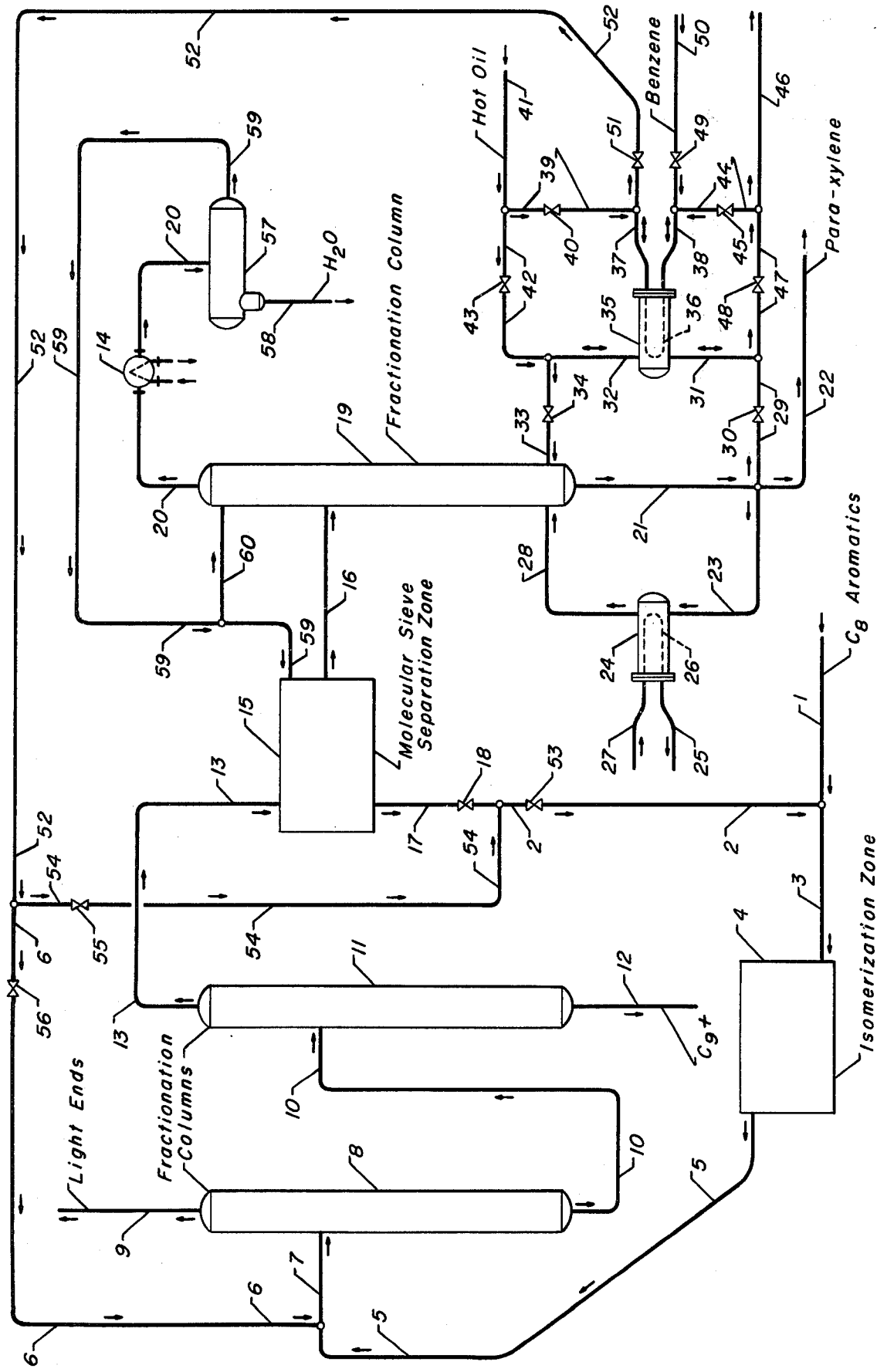

METHOD FOR DRYING A HYDROCARBON CONVERSION APPARATUS

FIELD OF THE INVENTION

The invention relates to a method of starting up a hydrocarbon or mineral oil conversion process which utilizes a fractionation column. It more specifically relates to those processes in which the amount of material to be fractionated in the column justifies the use of two or more reboilers and in which process it is necessary or desirable to remove water or other vaporizable materials from the apparatus prior to performing the process. In the preferred embodiment the fractionation column is used to purify alkylaromatic hydrocarbons as part of a process utilizing a bed of molecular sieves to separate alkylaromatic hydrocarbons, and benzene is vaporized to form a superheated drying vapor.

PRIOR ART

In a great many processes it is necessary to prevent or limit the contact of the reactants, catalyst or separatory material with water or some other vaporizable material. This may be because of the deactivating or destructive effect of water on a solid catalyst or to limit contamination or side reactions in the products or feed streams. This water may be present due to condensation, spillage, precipitation or from previous operation of the process. In a new or revamped plant the presence of water vapor and trapped liquid water which cannot be drained is a relative certainty.

Those skilled in the art have recognized the need to remove this water and therefore have developed various "startup" methods which include one or more steps designed to remove water from the apparatus. These methods vary from process to process depending on equipment configurations and other variables such as catalyst and reactant composition. A common method to remove water or other liquids, such as solvents or regeneration media, from an apparatus comprises passing a superheated vapor through the apparatus. This vapor is maintained at a sufficient temperature to effect the vaporization of the undesired liquids. The vapor is discharged into a condenser or other means which allows the separation and recovery of the various materials. This superheated vapor may in some instances be any readily available hydrocarbon or steam. Steam is not acceptable for use with some materials such as molecular sieves. Heretofore, the vapor stream was often produced in a separate heater which may have been provided exclusively for this purpose. An alternative prior art method comprises the use of heaters on other downstream process units which will not be brought on-stream until the subject process is operating.

A reduction in the capital cost of hydrocarbon conversion processes by the multipurpose utilization of reboiler heaters has been presented in the prior art. U.S. Pat. No. 3,873,440 (Cl. 208-108) presents a startup procedure for hydrocarbon conversion processes wherein the heater used to reboil a product fractionator is initially used to heat a recirculated reactant stream instead. This reactant stream is continuously heated and recycled through a catalytic reaction zone until a high temperature exothermic reaction begins to occur in the reaction zone at a rate which evolves sufficient heat to maintain the reaction without any external heat input. The heater is then utilized in its customary role as a reboiler.

DETAILED DESCRIPTION

The startup procedure for many commercial hydrocarbon conversion processes include a step wherein the various process vessels, transfer lines and other equipment forming the conversion apparatus is dried. This step may be performed in processes utilizing a bed of a solid catalyst which is sensitive to water, such as the halogen containing catalysts often used in a paraffin isomerization or aromatic hydrocarbon alkylation process. It may also be performed as part of the startup procedure in processing units utilizing a liquid catalyst such as hydrogen fluoride or sulfuric acid. Drying of the processing unit is also required when a moisture sensitive adsorbent is utilized within the process. A common example of this are the various molecular sieves used to separate hydrocarbons. Such processes include the simulated moving bed processes used to separate para-xylenes from other xylenes as described in U.S. Pat. Nos. 3,696,107; 3,626,020 and 3,201,491. Processes specific to the separation of other hydrocarbons including olefins, paraffins, ethylbenzene, pinenes, etc. will normally at least to some extent require a drying step in their startup procedure. The subject method will be utilitarian in any of these processes which include a multireboiler fractionation column for the purification of a product stream. The method also has utility for the removal of other vaporizable liquids from a hydrocarbon conversion apparatus.

It is an objective of this invention to provide a method of drying a hydrocarbon conversion apparatus which comprises at least one process vessel, fluid transfer lines and a fractionation column. It is another objective of this invention to lower the construction costs of this apparatus by eliminating the need for a heater used solely for generating a superheated vapor for drying.

These objectives are obtained by the subject method, which may be briefly described as generating a superheated vapor stream in the tubes of one of a plurality of horizontal tube and shell thermosyphon reboilers connected to the bottom of a fractionation column and passing this vapor stream through the process vessels and lines which are to be dried for a sufficient amount of time to adequately dry these vessels and lines, while simultaneously generating a second vapor stream on the shell side of a second reboiler and passing this second vapor stream into the fractionation column. When the apparatus is sufficiently dry, the flow of the heating fluid is changed from the shell side to the tube side of the first reboiler, and it is used to generate vapors which are passed into the fractionation column in a manner similar to the second reboiler.

The preferred embodiment of the invention is shown in the Drawing. For purposes of illustration, it is assumed the inventive concept is being used in conjunction with a process for the production of para-xylene. Other embodiments of the invention are not illustrated, but this is not intended to limit the scope of the invention to this specific example or to use with this specific process. For purposes of simplicity and clarity many needed subsystems such as controls, sensors and internal vessel equipment which do not in themselves form part of the inventive concept have been deleted.

Referring now to the Drawing, during normal on-stream operations a hydrocarbon stream comprising a mixture of $C_8$ aromatics and possibly other aromatics enters the process through line 1. It is admixed with a recycle stream from line 2 and passed into isomerization zone 4 through line 3. The isomerization zone functions to produce an equilibrium concentration of each of the xylene isomers in an isomerate stream removed through line 5. The isomerization zone contains a suitable system for the separation of hydrogen and other light gases which are to be recycled from the isomerate stream, and the isomerate stream therefore contains basically only $C_5+$ material. The isomerate stream is passed through line 7 into a first fractionation column 8. This column is operated under conditions effective to cause the removal of light ends, such as $C_5$–$C_7$ hydrocarbons, as an overhead stream removed in line 9. The remaining portion of the isomerate stream is removed from the bottom of the fractionation column in line 10 and passed into a second fractionation column 11. The second fractionation column is operated under conditions which are effective to remove $C_9+$ hydrocarbons from the remaining portion of the isomerate stream. This fractionation is performed because of the detrimental effect of $C_9$ aromatics on the typical molecular sieve used in the downstream separation zone 15.

By this series of fractionation steps there is produced an overhead stream removed in line 13 which is very rich in $C_8$ aromatic hydrocarbons including all three xylene isomers. This overhead stream is condensed in an overhead system not shown and then passed as a liquid through line 13 into the molecular sieve separation zone 15. The $C_8$ aromatics may alternatively be withdrawn from the column as a liquid sidecut. This separation zone is preferably a simulated moving bed system similar to that previously referred to. It is operated under conditions effective to cause the selective removal of para-xylenes from the overhead stream. The remaining portion of the overhead stream is removed in line 17 as a raffinate stream and passes through valve 18 to the junction with line 54. The raffinate stream is then recycled through valve 53 in line 2 to the isomerization zone.

A separation zone product stream comprising para-xylene and a desorbent, such as toluene or para-diethyl-benzene, is removed from the separation zone in line 16 and passed into a third fractionation column 19. This fractionation column is operated under conditions effective to remove the desorbent from the product stream. The desorbent exits the fractionation column in line 20 and is collected in overhead receiver 57 after condensation in cooler 14. Liquid phase desorbent returns to the separation zone in line 59. Reflux may be fed to the column via line 60. A bottoms liquid stream comprising essentially pure paraxylene is removed from the third fractionation column in line 21. A net bottoms product stream is withdrawn from the process in line 22 at a rate which preferably is set by a level control means operatively associated with the bottom of the fractionation column.

During normal on-stream operation two separate portions of the bottoms stream in line 21 are diverted into two different thermosyphon reboilers 35 and 24. The first portion is diverted through line 29 and passes through valve 30 to line 31, which directs this stream into a first reboiler 35. This xylene stream is vaporized by indirect heat exchange against the hot oil stream passing through a bundle of U-shaped heat exchange tubes 36. The hot oil stream enters the process through lines 41 and 39, and passes through open valve means 40. It then enters the first reboiler means through line 37, passes through the tubes 36 and exits the reboiler through line 38. For simplicity only one of the plurality of tubes is illustrated. At this time valve 45 is open, allowing the hot oil stream to leave the process through lines 44 and 46. Valve 48 in line 47 is closed at this time. The xylene vapor stream formed in this manner is removed from the reboiler in line 32 and passed through line 33 and open valve 34 to the bottom of the fractionation column. Valve 43 in line 42 is closed at this time. Valves 49 and 51 are also closed during this normal on-stream operation.

The second diverted portion of the bottoms stream is passed through line 23 to the shell side of the reboiler 24. It therein contacts a bundle of U-tube heat exchangers 26 through which a stream of hot oil is circulated via lines 27 and 25. A second xylene vapor stream formed in this manner is removed from the reboiler and passed into the bottom of the fractionation column through line 28.

The above description illustrates the normal on-stream operation of the subject process. As with all processing units, it will occasionally be shut down for normal, periodic maintenance and examination. The shut down of the unit may also be dictated by the shut down of up-stream operations which generate the $C_8$ aromatics, or it may be necessary to shut down the isomerization zone for the replacement of deactivated catalyst. It is customary to schedule the performance of any necessary regular maintenance on the other elements of the process apparatus at this time in an effort to avoid the necessity of shutting down the process at some other undesired time. It is therefore to be expected that besides the necessary unsealing of the apparatus, such as the opening of the isomerization zone for the replacement of catalyst, there will also occur the examination of fractionation column internals, heat exchange tubes, control elements and valves, etc. Each of these openings of the process apparatus provides an occasion for the entrance of moisture. It is necessary to perform a drying step before the process is once again placed on-stream. It is also normally necessary to perform a drying step when the unit is initially placed on-stream immediately following its construction. During such an initial startup, it may be expected that sizable quantities of water have collected due to condensation or precipitation and have been trapped in various process vessels or lines. It must also be remembered that a sizable amount of water is present in the air which initially fills these vessels and lines. The subject drying method may be utilized in either of these two situations.

The drying of the entire process apparatus is normally only one of several preparatory steps in the startup of a process. It may be preceded by such steps as acidizing, purging and pressure testing. During these steps, and the subject drying steps, the apparatus may contain whatever catalyst and absorbent which will be utilized during the process, but it will not contain the hydrocarbon feed material. That is, during the drying step, the $C_8$ aromatic stream will not be fed into the process described above, and $C_8$ aromatics will not be present in any of the fractionation columns or their associated fluid transfer lines.

Preparatory to the drying step valve 43 in line 42 will be opened to allow passage of the hot oil stream to the shell side of the first reboiler 35. Valves 40 and 34 will be closed prior to opening valve 43. The oil will be removed from the reboiler through line 31 and passed through line 47 through open valve 48 to line 46. Valves 45 and 30 will at this time be in a closed position. This first reboiler is thus isolated from the fractionation column by closed valve 34 in the vapor transfer line 33 and closed valve 30 in liquid transfer line 29. In the preferred embodiment, the hot oil is in this manner passed on the opposite side of the indirect heat exchange tubes utilized within the reboiler as compared to normal xylene vaporization operations. No changes are made in the normal flow of the bottoms liquid and the hot oil to the second reboiler means 24.

Valve 49 in line 50 is then opened to admit a startup stream comprising benzene to the tubes 36 of the first reboiler through intermediate transfer line 38. This benzene enters at a controlled rate and is exchanged against a sufficient quantity of high temperature hot oil that there is effected first vaporization and then the superheating of the benzene. The resultant superheated vapor stream is removed from the first reboiler through lines 37 and 52 through now open valve 51. It continues through line 52 to the junction with line 6. During the previously described on-stream operation, valve 56 is closed. In one embodiment of the invention all or a portion of the superheated vapor stream is passed into line 6. This stream is thereby directed to the junction with line 7 and into the first fractionation column 8. It may then be caused to continue through line 10 into the second fractionation column 11. If desired portions of this superheated stream may be vented through lines 9 and 12. However, it is preferred that all or substantially all of this vapor stream is removed overhead from the second fractionation column. At this point it is preferably condensed, with the condensate being drained from the overhead receiver, not shown, of column 11. This condensation step allows the monitoring of the rate of water removal since the water may be separated by decantation. The temperature of the column may also be monitored to assure total dryness. Alternatively, the vapor stream may be passed through line 13 into separation zone 15.

The exact drying sequence which is utilized in any specific process and also the sections of the process apparatus which are subject to the drying step will vary depending on such factors as the ability of the catalyst and any absorbent to withstand contact with superheated vapors or any resultant condensate. There are therefore different and alternative methods for drying specific process apparatus. As an example of an alternative method of performing the drying step, a portion or all of the superheated vapor passing through line 52 may be directed through line 54 through open valves 55 and 53. This stream would then be charged into line 2 and the isomerization zone 4. It may then be passed into the first fractionation column by itself or in conjunction with superheated vapors passing through line 6. This stream may then be directed in any of the various flows described above.

In the preferred embodiment of the invention a superheated benzene stream is passed through lines 54 and 17 to effect the partial drying of the molecular sieves employed in separation zone 15. This drying is necessary to maximize the separatory ability of the molecular sieves. This drying step may be conducted for a preset manner which has been found to provide a proper degree of drying by past experience. Alternatively, the effluent of the separation zone in line 16 can be monitored for its water content. The sieves are not totally dried since the desired water content for the sieves used in xylene separations is approximately 4 wt.%. The optimum water content may vary from this for different types of sieves. In other embodiments of the invention, such as the previously described drying of reaction zones or fractionators, the passage of the superheated vapor is normally continued until all liquid phase water has been removed. Since these vessels are being flushed by the superheated vapor, little if any water will remain in the vapor phase.

In the preferred embodiment the superheated vapor is passed through the separation zone 15 and then into a fractionation column such as column 11. This column is operated as a stripper with a bottoms stream being continuously removed from the column in lines 21 and 22. Overhead vapors comprising the startup liquid, benzene, and water are removed in line 20 and condensed in cooler 14. The two liquid phases which result from this are collected in the overhead receiver 57. The column is operated on total reflux and all of the benzene is returned to the column in lines 59 and 60. The water is removed in line 58. The rate of water removal from the conversion apparatus may therefore be monitored by observation of the rate of water removal in line 58. Vapors for the stripping of the water are formed by the vaporization of bottoms liquid in reboiler 24 in a manner similar to on-stream operation. That is, the benzene is vaporized on the outside (shell side) of the heat exchange tubes.

As the subject drying methods are basically an improvement on an already practiced step of normal startup procedures, those skilled in the art are fully cognizant of the conditions, apparatus and operational procedures which are required to regulate and control its performance. The temperatures, pressures, time periods and fluids utilized in the subject drying methods may be those which are now customarily used. In general, it is preferred that the fractionation column and the reboiler used to generate the superheated vapor are operated at a superatmospheric pressure in the range of from about 5 psig. to 260 psig. or higher, and preferably from 10 psig. to 100 psig. The startup liquid, a term intended to indicate a hydrocarbon having from 5 to 7 carbon atoms per molecule, is vaporized in the reboilers at a temperature about equal to its boiling point at the pressure imposed. It is then superheated about 5 to 100 Fahrenheit degrees, but preferably from 10 to 45 Fahrenheit degrees while still in the reboiler.

To accomplish this, it is normally necessary for the vapor to be confined to the tubes of a thermosyphon reboiler. In the normal mode of operation of a thermosyphon having a horizontal tube bundle, the type of reboiler which is preferred for use with the subject method, the heating fluid flows through the tubes. In the preferred embodiment the flow of the heating fluid is changed to the shell side of the reboiler during the vaporization of the startup liquid used to dry process vessels other than the fractionation column. This flow is again changed when this specific vaporization is terminated. As used herein the term "shell-side" is intended to refer to the volume and locations within the reboiler which are physically outside of the heat exchange tubes used within the reboiler. That is, a fluid stream passing through the shell-side of a reboiler may be indirectly heat exchanged against a heating fluid passing through the tubes of the reboiler.

In many situations the heat exchange surface area required in the reboiler becomes so sizable that it is preferable to divide the required area between two or more separate reboilers. A large column may therefore actually have three indirect heat exchangers which function as reboilers, with each having its own set of vapor and liquid transfer lines, etc. The subject drying method is limited in application to only those hydrocarbon conversion processes having large capacity fractionation columns which utilize more than one reboiler means.

As part of the subject method the reboiler used to dry the other process vessels is isolated from the fractionation column. As used herein this indicates that the reboiler remains attached to the column in the same manner as before, but the transfer lines which normally carry bottoms liquid from the column to the reboiler and vapor from the reboiler to the column are sealed by suitable valves. In the preferred embodiment, this isolated reboiler is not required to generate sufficient vapors for operation of the fractionation column. This is due in part to the lower heat of vaporization of the $C_5$–$C_7$ startup liquid compared to the $C_7$–$C_{12}$ product stream which is normally fractionated in the column. In addition, the startup liquid vaporizes at a lower temperature which increases the available mean temperature differential across the reboiler when a heating fluid of the same temperature is used in both the drying and onstream operational modes. These two factors combine to reduce the surface area required for the vaporization of the startup liquid to the extent that one of the two or more reboilers used on the column is not required during the startup procedure.

The preferred embodiment of the invention may be characterized as a method of drying a hydrocarbon conversion apparatus comprising a fractionation column, a process vessel containing a bed of molecular sieves and liquid transfer lines and used to perform a hydrocarbon conversion process in which a product stream comprising xylene is fractionated which comprises the steps of passing a first startup stream comprising benzene and which is an effluent stream of the process vessel being dried into the fractionation column, there being a first and a second shell and tube reboiler operatively associated with the fractionation column, isolating the first reboiler from the fractionation column by sealing a liquid transfer conduit and a vapor transfer conduit connecting the first reboiler to the fractionation column, vaporizing a portion of the startup stream in the second reboiler to form a first vapor stream which is passed into the fractionation column, passing a high temperature heat transfer fluid stream across the outside of the tubes of the first reboiler while passing a second startup stream comprising benzene through the tubes to effect the vaporization and superheating of the second startup stream and the formation of a second vapor stream, and passing the second vapor stream through the process vessel to effect the drying of the process vessel, terminating the vaporization of the second startup stream when the process vessel has been adequately dried, terminating passage of the second startup stream through the tubes of the first reboiler, and unsealing the liquid and the vapor transfer conduits, and terminating the flow of the first startup stream into the fractionation column and initiating flow of the product stream into the fractionation column, passing the high temperature heat transfer fluid stream through the tubes of the first reboiler, generating a third vapor stream comprising the xylene in the first reboiler and passing the third vapor stream into the fractionation column.

I claim as my invention:

1. A method of drying a hydrocarbon treating apparatus comprising a fractionation column, a process vessel and liquid transfer lines and which is used to perform a hydrocarbon treating process in which a product stream comprising a hydrocarbon having from 7 to 12 carbon atoms per molecule is fractionated which comprises the steps of:
   (a) passing a startup stream comprising a preselected hydrocarbon having from 5 to 7 carbon atoms per molecule into the fractionation column used in the hydrocarbon treating process, there being a first and a second reboiler operatively associated with the fractionation column;
   (b) isolating the first reboiler from the fractionation column by sealing a liquid and a vapor transfer line connecting the first reboiler to the fractionation column;
   (c) vaporizing a portion of the startup stream in the second reboiler to form a first vapor stream which is passed into the fractionation column;
   (d) passing a high temperature heat transfer fluid stream through the first reboiler and effecting the vaporization of a liquid stream comprising the preselected hydrocarbon which is simultaneously passed into the first reboiler to form a second vapor stream, superheating the second vapor stream and passing the second vapor stream through a process vessel other than the fractionation column to effect the drying of the process vessel;
   (e) terminating the vaporization of the liquid stream and the formation of the second vapor stream when the process vessel has been adequately dried, terminating the passage of the liquid stream into the first reboiler, unsealing the liquid and the vapor transfer lines connecting the first reboiler to the fractionation column, and terminating the passage of the startup stream into the fractionation column; and,
   (f) initiating the flow of the product stream into the fractionation column and the use of the first reboiler to generate a third vapor stream which is passed into the fractionation column.

2. The method of claim 1 further characterized in that the preselected hydrocarbon is benzene.

3. The method of claim 1 further characterized in that the process vessel is a second fractionation column.

4. The method of claim 1 further characterized in that the product stream contains aromatic hydrocarbons having from 7 to 9 carbon atoms per molecule and is produced in the hydrocarbon treating process.

5. The method of claim 1 further characterized in that the process vessel contains a bed of molecular sieves used for separating hydrocarbons.

6. A method of drying a hydrocarbon treating apparatus comprising a fractionation column, a process vessel and liquid transfer lines and used to perform a hydrocarbon treating process in which a product stream comprising an aromatic hydrocarbon having from 7 to 12 carbon atoms per molecule is fractionated which comprises the steps of:
   (a) passing a first startup stream comprising a preselected hydrocarbon having from 5 to 7 carbon atoms per molecule into the fractionation column, there being a first and a second shell and tube reboiler operatively associated with the fractionation column;
   (b) isolating the first reboiler from the fractionation column by sealing a liquid transfer conduit and a vapor transfer conduit connecting the first reboiler to the fractionation column;

(c) vaporizing a portion of the startup stream in the second reboiler to form a first vapor stream which is passed into the fractionation column;

(d) passing a high temperature heat transfer fluid stream across the outside of the tubes of the first reboiler while passing a second startup stream comprising the preselected hydrocarbon through the tubes to effect the vaporization and superheating of the second startup stream and the formation of a second vapor stream, and passing the second vapor stream through the process vessel to effect the drying of the process vessel;

(e) terminating the vaporization of the second startup stream when the process vessel has been adequately dried, terminating passage of the second startup stream through the tubes of the first reboiler, and unsealing the liquid and the vapor transfer conduits; and, (f) terminating the flow of the first startup stream into the fractionation column and initiating flow of the product stream into the fractionation column, passing the high temperature heat transfer fluid stream through the tubes of the first reboiler, generating a third vapor stream in the first reboiler and passing the third vapor stream into the fractionation column.

7. The method of claim 6 further characterized in that the aromatic hydrocarbon is a xylene.

8. The method of claim 6 further characterized in that the hydrocarbon treating process includes the separation of hydrocarbons through the use of molecular sieves.

9. The method of claim 8 further characterized in that the hydrocarbon treating process includes the isomerization of aromatic hydrocarbons.

10. The method of claim 9 further characterized in that the first and the second startup streams comprise benzene.

11. The method of claim 8 further characterized in that the first startup stream comprises an effluent stream of the process vessel which is being dried and the process vessel contains a bed of the molecular sieves.

* * * * *